United States Patent
Maiorana et al.

[11] Patent Number: 5,705,657
[45] Date of Patent: Jan. 6, 1998

[54] ISOCYANATE PROCESS FOR THE PREPARATION OF 1,3A,8-TRIMETHYL-1,2,3, 3A, 8, 8A-HEXAHYDRO-PYRROLE [2,3-B] INDOL-5 (3AS, 8AR) -HEPTHYLCARBAMATE

[75] Inventors: Stefano Maiorana; Anna Bonura; Giorgio Chiodini, all of Milan, Italy

[73] Assignee: Labochim Laboratorio Chimico Internazionale S.p.A., Milan, Italy

[21] Appl. No.: 416,572

[22] Filed: Apr. 4, 1995

Related U.S. Application Data

[63] Continuation-in-part of Ser. No. 104,163, PCT/EP92/00278 filed on Feb. 10, 1992.

[30] Foreign Application Priority Data

Feb. 14, 1991 [IT] Italy .................... MI91A0388

[51] Int. Cl.[6] .................................. C07D 487/04
[52] U.S. Cl. ...................................... 548/429
[58] Field of Search ................................ 548/429

[56] References Cited

PUBLICATIONS

Segre, Pharmacological Research 25, 139(1992).
Marta, Life. Sci 43, 1921(1988).
Unni, J Chromatog. 573, 275(1991).
Ogare, Brain Res 589, 307 (1992).
Linville, J Neurosci Res. 31 573(1992).
Rapniak, J Neurological Sci 107, 246(1992).
Thompson, New Eng J. Med. 323, 445(1990).

*Primary Examiner*—Mark L. Berch
*Attorney, Agent, or Firm*—Guido Modiano; Albert Josif; Daniel J. O'Byrne

[57] ABSTRACT

A process for the preparation of 1,3a,8-trimethyl-1,2,3,3a, 8,8a-hexahydro-pyrrole[2,3-b]indol-5(3aS,8aR)-heptylcarbamate, of formula (I)

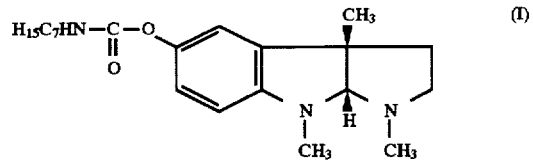

by reacting eseroline with heptylisocyanate in the presence of a metal cyanate and of a quaternary ammonium salt, in polar aprotic solvents.

13 Claims, No Drawings

ISOCYANATE PROCESS FOR THE PREPARATION OF 1,3A,8-TRIMETHYL-1,2,3, 3A, 8, 8A-HEXAHYDRO-PYRROLE [2,3-B] INDOL-5 (3AS, 8AR) -HEPTHYLCARBAMATE

This application is a Continuation-In-Part of U.S. Ser. No. 08/104,163 filed Aug. 11, 1993 which is a 371 of PCT/EP92/00278.

The present invention relates to a process for the preparation of 1,3a,8-trimethyl-1,2,3,3a,8,8a-hexahydropyrrole[2,3-b]indol-5(3aS,8aR)-heptylcarbamate of formula (I):

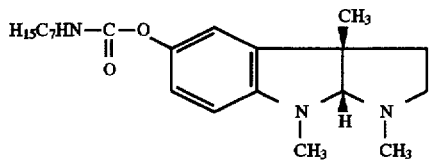

Said compound, which is known under the International Nonproprietary Name "heptastigmine", and methods for the preparation thereof, are disclosed in Italian Patent Applications N. 47780 A/84 and 19964 A/87. The compound has interesting pharmacological properties because it exhibits acetylcholinesterase inhibition activity and is less toxic than physostigmine. The organic salts of the physostigmine derivatives have already been patented in U.S. Pat. No. 4,978,673 and a pharmaceutical composition containing heptastigmine is claimed in claim 8 of this patent.

According to the above cited Patent Applications, heptastigmine (I) can be obtained starting from eseroline (II)

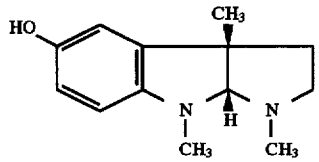

by treatment either with phosgene and heptylamine, or with heptylisocyanate. The latter method allows to obtain higher yields than the first one, as far as the reaction is carried out in an ether solution and in the presence of metal sodium.

Said methods, however, suffer form evident drawbacks, particularly on industrial scale. In fact, the first method involves the use of highly toxic phosgene, whereas the second one suffers from hazards of fires and explosions, connected to the use of ether and metal sodium.

Now, it has surprisingly been found that heptastigimine (I) can be obtained in very good yields and high purity, by reacting eseroline (II) with heptylisocyanate in the presence of a) catalytic amounts of a quaternary ammonium or salt, $R^1R^2R^3R^4N^+X^-$, or phosphonium salt, $R^1R^2,R^3,R^4,P^+X^-$, and b) catalytic amounts of a metal cyanate, in a polar aprotic solvent, according to the scheme reported hereinbelow:

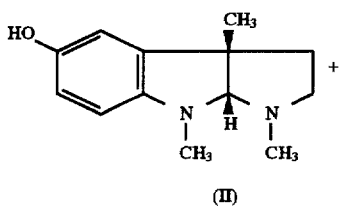

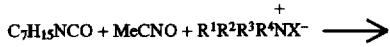

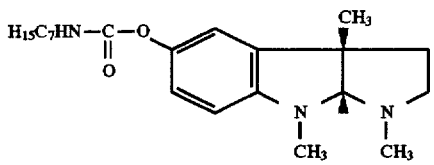

wherein Me is an alkali metal or the equivalent of an alkaline-earth metal, and preferably potassium; $R_1$–$R_4$, which can be the same or different, are $C_1$–$C_{12}$ alkyl or aralkyl, preferably ethyl or n-butyl; X is an anion, preferably chlorine or bromine.

The molar ratio of eseroline to heptylisocyanate is comprised between 1:1 and 1:5, preferably between 1:1 and 1:1.2. Heptylisocyanate amounts which are in excess or defect with respect to the preferred range can also be used, but no advantages are obtained.

The molar ratio of eseroline to metal cyanate can range between 1:0.5 and 1:0.01, preferably between 1:0.4 and 1:0.1, whereas the molar ratio of eseroline to quaternary ammonium or phosphonium salt is comprised between 1:0.6 and 1:0.05, preferably between 1:0.5 and 1:0.2.

Acetonitrile and ethyl acetate are preferably used as the polar aprotic solvent.

It has also been found that metal alcoholates, particularly potassium t-butylate, may substitute in some cases the metal cyanate.

The reaction is preferably carried out under nitrogen, in order to prevent eseroline oxidation, and at temperatures comprised between 0° C. and 40° C., preferably at about 20° C. The order in which reagents are added is not particularly critic; however heptylisocyanate, optionally diluted with the solvent, is preferably added to a solution or suspension of eseroline, metal cyanate and quaternary ammonium or phosphonium salt in the solvent itself. At the end of the reaction (the progress of which can be followed with chromatographic methods, for example by TLC mix, eluent $CH_2Cl_2$/MeOH 9:1) solvent is evaporated under reduced pressure, the residue is taken up with toluene, the unsolubles are filtered off and the toluene solution is repeatedly washed with water. Toluene is evaporated off to obtain the desired product as a viscous oil, which is left to crystallize or is transformed into the corresponding tartrate, according to indications of Italian Patent Application N. 19964 A/87.

According to an alternative route, eseroline can be N-heptylcarbamoylated with heptylisocyanate which is prepared in situ starting from a 1-haloheptane (preferably 1-bromoheptane) and a metal cyanate (preferably potassium cyanate) in the presence of a quaternary ammonium or phosphonium salt, in polar aprotic solvents, preferably acetonitrile. In this case the reaction is carried out (always under nitrogen protection) at the reflux temperature of the mixture; compound (I) is then recovered as described above.

The following Examples further illustrate the invention.

EXAMPLE 1

500 g (2.3 moles) of eseroline are dissolved in 20 l of anhydrous acetonitrile, under nitrogen; 37 g (0.46 mole) of potassium cyanate and 148 g (0.69 mole) of tetraethylammonium bromide are added thereto and, at 19°–20° C., a solution of 325 g (2.5 moles) of heptylisocyanate in 20 l of anhydrous acetonitrile is quickly dropped therein. The reaction mixture is kept under stirring for 8 hours, then the insolubles are filtered off, solvent is evaporated off under reduced pressure, the residue is taken up into 100 l of toluene and the toluene solution is washed with 6×100 l of water.

Toluene is evaporated under vacuum to yield a yellowish viscous oil which undergoes solidification and can be transformed into the corresponding tartrate according to the indications of Italian Patent Application n. 19964 A/87. Yield 90%.

EXAMPLE 2

150 g of eseroline (0.69 mole), 83.9 g of potassium cyanate (1.035 moles), 148 g of 1-bromoheptane (0.83 mole) and 29 g of tetraethylammonium bromide (0.14 mole) are placed into 5 l of anhydrous acetonitrile. The reaction mixture is refluxed for 19 hours, the insolubles are filtered off and the mixture is worked up as described in Example 1. Heptastigmine yield is 63%.

EXAMPLE 3

The procedure of Example 1 is followed, but replacing tetraethylammonium bromide with an equivalent amount of tetra-n-butylammonium bromide. The yield is still 90%.

EXAMPLE 4

The same results as those of Example 2 are obtained using n.Bu$_4$NBr$^-$ instead of (C$_2$H$_5$)$_4$NBr$^-$, the other reaction conditions being unchanged.

EXAMPLE 5

The same results as those of Example 2 were obtained using 0.14 mole tributyl hexadecyl phosphonium bromide instead of tetraethylammonium bromide.

We claim:
1. A process for the preparation of 1,3a,8-trimethyl-1,2,3,3a,8,8a-hexahydro-pyrrole[2,3-b]indol-5(3aS,8aR)-heptylcarbamate of formula (I):

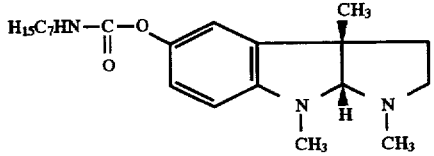

characterized in that eseroline (II) is reacted with heptylisocyanate in the presence of a) catalytic amounts of either a quaternary phosphonium salt R$^1$R$^2$R$^3$R$^4$P$^+$X$^-$ quaternary ammonium salt R$^1$R$^2$R$^3$R$^4$N$^+$X$^-$, wherein R$^1$, R$^2$, R$^3$ and R$^4$ can be the same or different and are C$_1$–C$_{12}$ alkyl or aralkyl and X is an anion, and b) catalytic amounts of a metal cyanate (MeOCN), wherein Me is an alkali metal or the equivalent of an alkaline-earth metal, in a polar aprotic solvent, according to the following scheme:

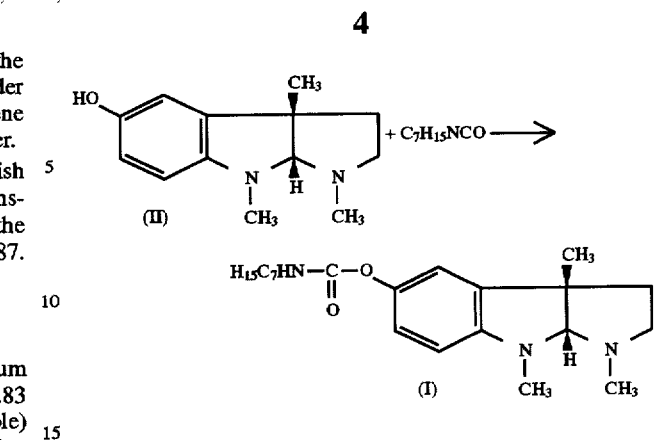

2. A process according to claim 1, characterized in that the molar ratio of eseroline to heptylisocyanate is between 1:1 and 1:5.

3. A process according to claim 1, characterized in that the molar ratio of eseroline to metal cyanate is between 1:0.5 and 1:0.01.

4. A process according to claim 1, characterized in that the molar ratio of eseroline to quarternary ammonium or phosphonium salt is between 1:0.6 and 1:0.05.

5. A process according to claim 1, characterized in that acetonitrile is used as the solvent.

6. A process according to claim 1, characterized in that the reaction is carried out at temperatures comprised between 0° C. and 40° C.

7. A process according to claim 1, characterized in that eseroline is reacted with heptylisocyanate which is prepared in situ starting from a 1-haloheptane and a metal cyanate in the presence of a quaternary ammonium salt, in the polar aprotic solvent.

8. A process according to claim 1, wherein Me is potassium; C$_1$–C$_{12}$ alkyl is ethyl or n-butyl; X is chlorine or bromine.

9. A process according to claim 7, wherein the 1-haloheptane is 1-bromoheptane and the metal cyanate is potassium cyanate.

10. A process according to claim 7, wherein the polar aprotic solvent is acetonitrile.

11. A process according to claim 4, characterized in that the molar ratio of eseroline to quarternary ammonium or phosphonium salt has a value between 1:0.5 and 1:0.2.

12. A process according to claim 2, characterized in that the molar ratio of eseroline to heptylisocyanate has a value between 1:1 and 1:1.2.

13. A process according to claim 3, characterized in that the molar ratio of eseroline to metal cyanate has a value between 1:0.4 and 1:0.1.

* * * * *